United States Patent

Oette et al.

[11] 4,221,732
[45] Sep. 9, 1980

[54] STRUCTURAL ANALOGS OF NATURAL PHOSPHOLIPIDS

[75] Inventors: Kurt Oette, Cologne; Tschae S. Tschung, Rodenkirchen, both of Fed. Rep. of Germany

[73] Assignee: A. Nattermann & Cie. GmbH, Fed. Rep. of Germany

[21] Appl. No.: 38,354

[22] Filed: May 11, 1979

[30] Foreign Application Priority Data

May 12, 1978 [DE] Fed. Rep. of Germany ....... 2820893

[51] Int. Cl.$^3$ .......................... C07F 9/02; C11C 3/00; A23J 7/00
[52] U.S. Cl. .................................. 260/403; 260/944; 260/945
[58] Field of Search ................... 260/403, 944, 945

[56] References Cited

U.S. PATENT DOCUMENTS

| | | | |
|---|---|---|---|
| 3,960,905 | 6/1976 | Eibl et al. | 260/403 |
| 3,985,875 | 10/1976 | Hayashi et al. | 260/403 |
| 4,098,849 | 7/1978 | Redmore et al. | 260/944 |

Primary Examiner—John F. Niebling
Attorney, Agent, or Firm—Karl W. Flocks

[57] ABSTRACT

Structural analogs of natural phospholipids of the general formulae

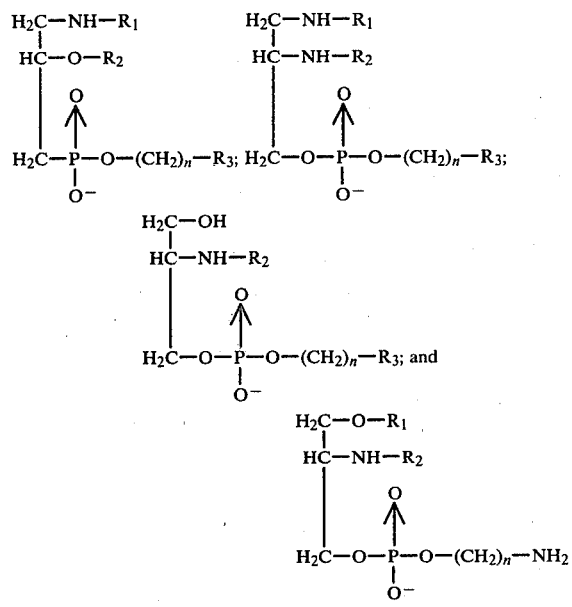

where $R_1$ and $R_2$ represent either hydrogen and/or saturated or unsaturated straight-chain and branched acyl radicals with 2 to 24 C-atoms and $R_3$ an amino group or a substituted amino group of the formula

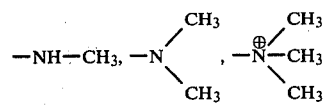

and n is a number from 1–3, are useful in the preparation of stable liposomes useful as vehicles for pharmaceutical preparations.

2 Claims, No Drawings

STRUCTURAL ANALOGS OF NATURAL PHOSPHOLIPIDS

This invention relates to new, pharmacologically effective, structurally related synthetic analogs of natural phosphatides. The acyl radicals are derived preferentially from naturally occurring fatty acids as, for example, palmitic, stearic, oleic, linoleic, linolenic, and arachidonic acid, all of which are contained in the usual phosphatides, as is well known.

The new phosphatides or phopholipids have the formulae:

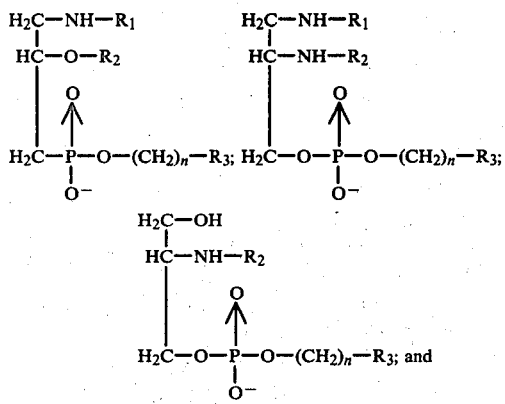

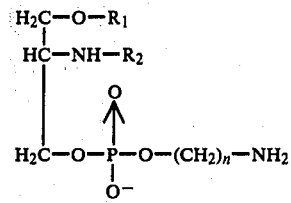

where $R_1$ and $R_2$ represent either hydrogen and/or saturated or unsaturated straight-chain and branched acyl radicals with 2 to 24 C-atoms and $R_3$ an amino group or a substituted amino group of the formula

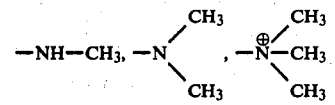

and n is a number from 1–3.

These new phosphatides which contain new amino or amide groups can be prepared easily synthetically from the corresponding monoamino propane diol or diamino propanol derivatives through the use of the synthetic processes and procedures well known for the synthesis of phosphatides.

To prepare the phospholipid analogs of this invention it is best to start with the corresponding compounds analogous to the diglycerides which contain a free OH-group in their molecule. Reaction of this functional group with suitable phosphoric acid halogenides produces at first the corresponding o-phosphoryl halogenides which are subsequently converted into the phosphatidylcholine or phosphatidyl ethanol amine analogs in accordance with the following general reaction diagrams:

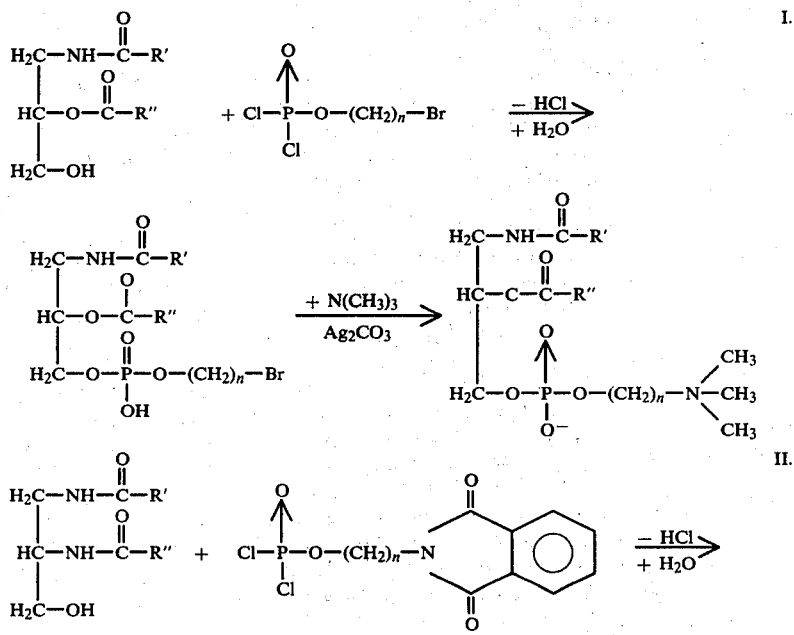

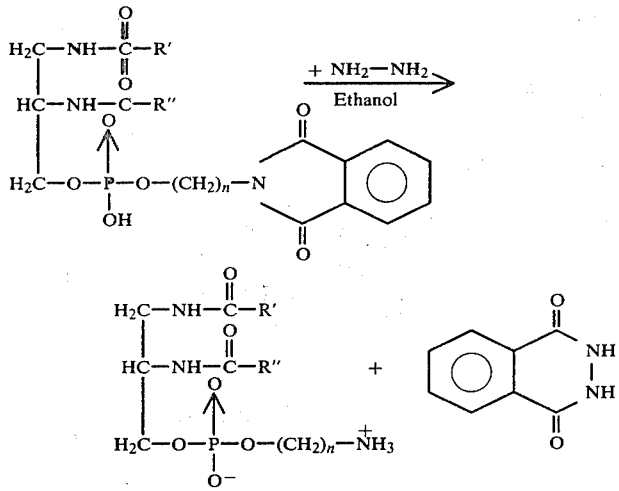

R', R" represent saturated or unsaturated alkene chains with primarily 15 to 21 carbon atoms.

For the preparation of the phospholipid analogs according to the invention, it is possible to use, for example, diglyceride analogs having the following general formulae:

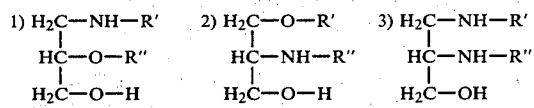

Here, R' and R" represent saturated or unsaturated, straight chain or branched carbonyl radicals having from 2 to 24 C-atoms, but preferentially radicals of natural fatty acids as, for example, palmitic-, stearic-, oleic-, linoleic-, linolenic-, or arachidonic acid.

The reaction of the diglyceride analogs takes place generally at temperatures between $-10°$ C. to $+60°$ C. in inert solvents like benene, hydrocarbons or chlorinated hydrocarbons and in the presence of an inert base like triethylamine or pyridine. The reaction process can be followed using thin layer chromatography. The purification of the phospholipid analogs according to the invention can be achieved through column chromatography.

In these new structural analogs of the naturally occurring phosphatides according to the invention, the fatty acids are attached either partially or totally by acid-amide like bonds instead of the usual ester bonding.

The new compounds can be used in all cases where the natural phosphatides are employed. The greater the stability of these new phospholipids according to this invention towards hydrolytic influences make them better suited for the preparation of stable liposomes, the use of which as vehicles for pharmaceutically active substances and enzymes have been gaining in importance.

In animal tests following oral and/or intravenous application, the analogs are deposited in the lipids of cellular membrane structures and in the lipids of plasma lipoproteins. In vivo the analogs can change in part from one into another. The distribution of the analogs between individual organs, subcellular structures and lipoproteins is determined not only by the basic structure, but usually quite importantly by the amide-like bonded fatty acids. The analogs show the metabolic characteristics of the corresponding natural phosphatides. But the metabolism of the analogs is modified in a definite way by the relative stability of the amide group with respect to metabolism. This explains the special pharmacokinetic-pharmacodynamic effects of the compounds of the invention. The pharmacological effects are being determined by the basic structure and the fatty acid component and, in a number of the substances, additionally by the manner of application. Thus, they are quite differently defined.

In detail, the following characteristics are effected:
antilipemic
antiatherosclerotic
inhibition of tumor growth
suppression of immunity
retardation of blood platelet aggregation
antiprostaglandin For any particular compound, these effects are determined by routine, standard testing.

The following non-limitative examples are offered to better describe the invention:

EXAMPLE 1

100 mg (0.175 mMol) 1-N-palmityl-2-O-linolyl-1-amino-propane (diol-(2,3) are dissolved in 5 ml absolute chloroform and added dropwise to 63 mg (0.35 mMol) $\beta$-bromoethylphosphoric acid dichloride in 20 ml distilled chloroform and 2 ml pyridine in an icebath. After the reaction has stopped (after about 1 hour, DC-test) water is added and the solvent drawn off in a vacuum using ethanol and toluene. The reaction product, 1-N-palmityl-2-O-linolyl-1-amino-propane diol-(2,3)-3-phosphoryl-$\beta$-bromoethyl ester is purified column-chromatographically over silica. 130 mg of this are dissolved in 5 ml toluene, reacted with 0.5 ml trimethylamine in a thick-walled ampule and heated for about 10 hours at 60° C. The toluene is removed in a vacuum, the residue dissolved in 20 ml methanol, reacted with 0.5 g $Ag_2CO_3$ and left standing for 30 minutes at 50° C. while shaking occasionally. The silver salts are filtered off, the filtrate is evaporated in a vacuum and purified through column chromatography.

Yield: 117 mg=89% of the theory 1-N-palmityl-2-O-linolyl-1-amino-propane diol-(2,3)-3-O-phosphoryl-choline Rf-value: 0.40
CHCl$_3$/CH$_3$OH/H$_2$O (65:25:4)
MW: 757
Phosphorus analysis: calculated 4.095% P; found 4.11% P.

EXAMPLE 2

100 mg (0.21 mMol) 1-N-capryl-2-O-linolyl-1-amino-propane diol-(2,3) are dissolved in 5 ml absolute chloroform and added dropwise to 76 mg (0.42 mMol)β-bromoethyl phosphoric acid dichloride in 20 ml distilled chloroform and 2 ml pyridine in an icebath. After the reaction has stopped (about 1 hour, DC test) water is added and the solvent drawn off in a vacuum using ethanol and toluene. The reaction product, 1-N-capryl-2-O-linoly-1-amino propane diol-(2,3)-3-O-phospharyl-β-bromo ethyl ester is purified column-chromatographically over silica.

130 mg of this are dissolved in 5 ml toluene, reacted with 0.5 g Ag$_2$CO$_3$ and left standing for 30 minutes at 50° C. while shaking occasionally. The silver salts are filtered off, the filtrate is evaporated in a vacuum, dried in a high vacuum and purified through column chromatography.

Yield: 85% of the theory 1-N-capryl-2-O-linolyl-1-amino-propane diol-(2,3)-3-O-phosphoryl choline
Rf-value: 0.40
CHCl$_3$/CH$_3$OH/H$_2$O (65:25:4)
MW: 645
Phosphorus analysis: calculated 5.074% P; found 5.18% P.

EXAMPLE 3

200 mg (0.32 mMol) 1-N-palmityl-2-N-arachidonyl-1,2-diamino-propanol-(3) are dissolved in 10 ml absolute chloroform and added dropwise to 115 mg (0.64 mMol)β-bromoethylphosphoric acid dichloride in 30 ml distilled chloroform and 2 ml pyridine in an icebath. After the reaction has stopped (about 1 hour, DC-test) water is added and the solvent drawn off in a vacuum using ethanol and toluene. The reaction product, 1-N-palmityl-2-N-arachidonyl-1,2-diamino-propane-(3)-3-O-phosphoryl-β-bromoethyl ester is purified column-chromatographically over silica. The yield is 222 mg=85% of the theory.

The 222 mg thus obtained (0.28 mMol) are dissolved in 5 ml toluene, reacted with 1 ml trimethylamine in a thick-walled ampule and heated for about 10 hourse at 60° C. The toluene is removed in the vacuum, the residue is dissolved in 20 ml methanol, reacted with 0.5 g Ag$_2$CO$_3$ and left standing for 30 minutes at 50° C. while shaking occasionally. The silver salts are filtered off, the filtrate is evaporated in a vacuum, dried in a high vacuum and purified through column chromatography.

Yield: 191 mg=88% of the theory 1-N-palmityl-2-N-arachidonyl-1,2-diamino-propane-(3)-3-O-phosphoryl choline.
MW: 785
Rf-value: 0.41 CHCl$_3$/CH$_3$OH/H$_2$O)65: 25: 4)
Phosphorus analysis: calculated 3.972% P; found 4.13% P.

Using this method, the following compounds of the invention were prepared among others:

1-N-oleyl-2-O-linolyl-1-amino-propane diol-(2,3)-3-O-phosphoryl choline

Yield: 1.3 g=79% of the theory
MW: 787.5
Phosphorus analysis: calculated 3.937% P; found 4.01% P.
Rf-value: 0.39
CHCl$_3$/CH$_3$OH/H$_2$O (65:25:4)

1-N-stearyl-2-O-linolyl-1-amino-propane diol-(2,3)-3-O-phosphoryl choline

Yield: 1.45 g=82% of the theory
MW: 785.5
Phosphorus analysis: calculated 3.947% P; found 4.08% P.
Rf-value: 0.39
CHCl$_3$/CH$_3$OH/H$_2$O (65:25:4)

1-N-linolyl-2-O-linolyl-1-amino-propane diol-(2,3)-3-O-phosphoryl choline

Yield: 1.25 g=77% of the theory
MW: 781
Phosphorus analysis: calculated 3.969% P; found 3.85% P.
Rf-value: 0.40
CHCl$_3$/CH$_3$OH/H$_2$O (65:25:4)

1-N-palmityl-2-O-palmityl-1-amino-propane diol-(2,3)-3-O-phosphoryl choline

Yield: 1.65 G=85% of the theory
MW: 733
Phosphorus analysis: calculated 4.229% P; found 4.30% P.
Rf-value: 0.41
CHCl$_3$/CH$_3$OH/H$_2$O (65:25:4)

1-N-arachidonyl-2-O-linolyl-1-amino-propane diol-(2,3)-3-O-phosphoryl choline

Yield: 1.55 g =83% of the theory
MW: 805.5
Phosphorus analysis: calculated 3.849%; found 3.75% P.
Rf-value: 0.38 CHCl$_3$/CH$_3$OH/H$_2$O (65:25:4)

1-N-palmityl-2-O-oleyl-1-amino-propane diol-(2,3)-3-O-phosphoryl choline

Yield: 1.75 g=81% of the theory
MW: 763.5
Phosphorus analysis: calculated 4.060% P; found 3.95% P.
Rf-value: 0.40
CHCl$_3$CH$_3$OH/H$_2$ O (65:25:4)

1-N-stearyl-2-N-oleyl-1,2-diamino-propanol-(3)-3-O-phosphoryl choline

Yield: 1.45 g=79% of the theory
MW: 781
Phosphorus analysis: calculated 3.969% P; found 4.12% P.
Rf-value: 0.42
CHCl$_3$/CH$_3$OH/H$_2$O (65:25:4)

1-N-linoly-2-arachidonyl-1,2-diamino-propanol-(3)-3-O-phosphoryl-chlorine

Yield: 1.50 g=80% of the theory
MW: 804.5
Phosphorus analysis: calculated 3.853% P; found 3.71% P.
Rf-value: 0.41
CHCl$_3$/CH$_3$OH/H$_2$O (65:25:4)

EXAMPLE 4

At first 12.2 g (0.2 Mol) ethanolamine and 29.6 g (0.2 Mol) phthalic acid anhydride are heated slowly to 200° C. in an oil bath and kept at the temperature for 2–3 hours. After cooling to room temperature 150 ml ethanol are added and the mixture left standing over night. The crystallized reaction product is sucked off and recrystallized twice from ethanol. 18 g (0.09 Mol) of the N-phthalimidyl-ethanol amine thus obtained and 27.5 g (0.18 Mol) phosphorus-oxy-trichloride are dissolved in 100 ml absolute benzenl and the ecesss phosphorus-oxytrichloride is drawn off in a vacuum. The residue is dissolved in 100 ml absolute ether and left standing in an icebath. The chloride which has crystallized out as a white powder is sucked off, washed in absolute ether and dried.

100 mg (0.35 mMol) of the resulting dichloro phosphoric acid-N-phthalimidyl-ethylester in 20 ml distilled chloroform and 2 ml pyridine are prepared. In an ice bath 100 mg (0.175 mMol) 1-N-palmityl-2-O-linolyl-1-amino-propane diol-(2,3) in 5 ml absolute chloroform are added dropwise. The course of reaction is observed through thin layer chromatography. The reaction is interrupted after one hour through the addition of water, the solvent is drawn off in a vacuum with ethanol and toluene and the reaction product isolated through column chromatography.

100 mg (0.12 mMol) of the resulting 1-N-palmityl-2-O-linolyl-1-amino-propane diol-(2,3)-3-O-phosphoryl-(N-phthalimidyl)-ethanol amine are dissolved in 10 ml warm ethanol, reacted with 120 mg (0.24 mMol) hydrazine hydrate and left standing over night at room temperature. The mixture is acidified with dilute hydrochloric acid and the precipitate (phthalic acid hydrazide) sucked off. The ethanolic solution is neutralized with ammonia and extracted three times with chloroform.

Yield; 62 gm=73% of the theory 1-N-palmityl-2-O-linolyl-1-aminopropane diol-(2,3)-3-O-phosphorylethanolamine

MW: 715

Phosphorus analysis: calculated 4.336% P; found 4.36% P.

Rf-value: 0.60

ChCl$_3$/CH$_3$OH/H$_2$O (65:25:4)

EXAMPLE 5

149 mg (0.5 mMol) dichloro phosphoric acid-N-phthalimidyl-ethylester, prepared as described in Example 4, are set out in 20 ml distilled chloroform and 2 ml pyridine; in an icebath; 89 gm (0125 mMol) 1-N-oleyl-2-O-linolyl-1-aminopropane diol-(2,3) in 5 ml absolute chlorofrom are added dropwise. The course of the reaction is observed through thin layer chromatography. The reaction is interrrupted after 1 hour through the addition of water, the colvent is drawn off in a vacuum with ethanol and toluene and the reaction product isolated through column chromatography.

130 mg (0.15 mMol) of the resulting 1-N-oleyl-2-O-linoly-1-amino-propance diol-(2,3)-3-O-phosphoryl-(N-phthalimodyl)-ethanol amine are dissolved in 10 ml warm ethanol, reacted with 150 ml (0.30 mMol) hydrazine hydrate and left standing over night at room temperature. The mixture is acidificed with dilute hydrochloric acid and the precipitate (phthalic acid hydrazide) sucked off. The ethanolic solution is neutralized with ammonia and extracted three thime with chloroform.

Yield: 79 mg=71% of the theory 1-N-oleyl-2-O-linoly-1-aminopropane diol-(2,3)-3-O-phosphoryl-ethanolamine

MW: 744.5

Phosphorus analysis: calculated 4.16% P; found 3.85% P.

Rf-value: 0.60

ChCl$_3$/CH$_3$OH/H$_2$O (65:25:4)

The analogous process was followed in the preparation of 2-N-acyl-1-O-acyl-2-amino-propane diol-(2,3)-3-O-phosphoryl ethanol amine.

EXAMPLE 6

100 mg (0.175 mMol) 1-N-palmityl-2-N-linolyl-1,2-diamino-propanol-(3) are dissolved in 5 ml absolute chlorofrom and added dropwise to 104 mg (0.35 mMol) dichloro-phosphoric acid-N-phthalimidyl-ethyl ester in 20 ml distilled CHCl$_3$ and 2 ml pyridine in an icebath. The course of the reaction is tested after 1 hour through thin layer chromatography. The reaction is finally interrupted through the addition of H$_2$O and the solvent is sucked off in a vacuum with ethanol and toluene. The reaction product is isolated through column chromatography.

Yield: 73% of the theory 1,2-N-diacyl-1,2-diamino propanol-(3)-3-O-phosphoryl-(N-phthalimidyl)-ethanol amine 100 mg (0.12 mMol) 1-N-palmityl-2-N-linoly-1,2-diamino-propanol-(3)-3-O-phosphoryl-(N-phthalimidyl)-ethanol amine are dissolved in 10 ml warm ethanol, reacted with 12 mg (0.24 mMol) hydrazine hydrate and left standing over nigh at room temperature. Subsequently, it is acidified with dilute hydrochloric acid and the precipitate (phthalic acid hydrazide) is sucked off. The ethanolic solution is neutralized with ammonia and extracted three times with chloroform.

Yield: 77% of the theory=65 mg 1,2-N-diacyl-1,2-diamino propanol-(3)-3-O-phosphorylethanol amine

MW: 714

Rf-value: 0.45

CHCl$_3$/CH$_3$OH/H$_2$O (65:25:4)

Phosphorus analysis: calculated 4.342% P; found 4.28% P.

Among others, the following compound of this invention are prepared in an analogous way:

1-N-capryl-2-O-linolyl-1-amino-propane diol-(2,3)-3-O-phosphoryl-ethanol amine

Yield: 1.2 g=71% of the theory

MW: 602

Rf-value: 0.49

CHCl$_3$/CH$_3$OH/H$_2$O (65:25:4)

Phosphorus analysis: calculated 5.158% P; found 5.31% P.

1-N-stearyl-2-O-linolyl-1-amino-propane diol-(2,3)-3-O-phosphoryl-ethanol amine

Yield: 1.35 g=73% of the theory

MW: 742.5

Rf-value: 0.51

CHCl$_3$/CH$_3$OH/H$_2$O (65:25:4)

Phosphorus analysis: calculated 4.175% P; found 3.95% P.

2-N-linolyl-1-O-palmityl-2-amino-propane diol-(2,3)-3-O-phosphoryl-ethanol amine Yield: 2.5 g
MW: 713
Rf-value: 0.50
CHCl$_3$/CH$_3$OH/H$_2$O (65:25:4)
Phosphorus analysis: calculated 4.241% P; found 4.07% P.

2-N-arachidonyl-1-O-palmityl-2-amino-propane diol-(2,3)-3-O-phosphorylethanol amine Yield: 1.2 g = 75% of the theory
MW: 738
Rf-value: 0.53
CHCl$_3$/CH$_3$OH/H$_2$O (65:25:4)
Phosphorus analysis: calculated 4.20% P; found 4.43% P.

2-N-linolyl-1-O-linolyl-2-amino-propane diol-(1,3)-3-O-phosphoryl-ethanol amine Yield: 1.4 g = 70% of the theory
MW: 737
Rf-value: 0.51
CHCl$_3$/CH$_3$OH/H$_2$O (65:25:4)
Phosphorus analysis: calculated 4.20% P; found 4.38% P.

2-N-oleyl-1-O-oleyl-2-amino-propane diol-(1,3)-3-O-phosphoryl-ethanol amine

Yield: 0.9 g = 68% of the theory
MW: 750
Rf-value 0.48
CHCl$_3$/CH$_3$OH/H$_2$O (65:25:4)
Phosphorus analysis: calculated 4.133% P; found 3.86% P.

1-N-capryl-2-N-arachidonyl-1,2-diamino-propanol-(3)-3-O-phosphorylethanol amine Yield: 1.25 g = 75% of the theory
MW: 625.5
Rf-value: 0.48
CHCl$_3$/CH$_3$OH/H$_2$O (65:25:4)
Phosphorus analysis: calculated 4.956% P; found 4.73% P.

1-N-stearyl-2-N-oleyl-1,2-diamino-propanol-(3)-3-O-phosphoryl-ethanol amine

Yield: 1.07 g = 72% of the theory
MW: 748
Rf-value: 0.45
CHCl$_3$/CH$_3$OH/H$_2$O (65:25:4)
Phosphorus analysis: calculated 4.144% P; found 4.41% P.

EXAMPLE 7

For the preparation of the lysolecithin analogs or the cephalin analogs the following general method can be used: (a) enzymatic hydrolysis 202 μMol of a lecithin analog or of a cephalin analog are suspended in 30 ml borate buffer (pH = 7.4). To the suspension are added 10 mg lipase or phospholipase A$_2$ (depending on the analogous substance) and 30 ml peroxide-free ether. Lipolysis takes place within 3-4 hours at room temperature. 20 ml methanol are added to the aqueous solution and the fatty acid released is extracted 4 to 5 times with petrol ether (40°-60° C.). Subsequently the lyso-compound is extracted three times with chloroform from the aqueous phase. The solvent is removed through a rotating evaporator and the reaction product is finally dried over P$_2$O$_5$. Yield: about 40% of the theory (b) alkaline hydrolysis 100 mg (202 μMol) 1-N-palmityl-2-O-linolyl-1-amino-propane diol-(2,3)-3-O-phosphoryl-choline ester are dissolved in 10 ml 0.1 N KOH-methanyl and left standing at room temperature for 30-60 minutes. After adjustment of the pH to 3 with dilute hydroachloric acid, the methanolic solution is reacted with 10 ml water and the fatty acid released is extracted 4 to 5 times with petrol ether (40°-60° C.). Finally the lyso-compound is extracted three times from the aqueous phase with chloroform and the chloroform phases are put together and washed with water until neutral. The solvent is removed through a rotating evaporator and the residue dried over P$_2$O$_5$. Yield: 53 g = 81% of the theory

| formula | Lysolecithin analogs summation formula (MW) | Rf-value (running system) |
|---|---|---|
| CH$_2$—NH—C(=O)—R$_1$<br>CH—OH<br>CH$_2$—P(=O)(O$^\ominus$)—O—CH$_2$—CH$_2$—$^\oplus$N(CH$_3$)$_3$ | C$_{24}$H$_{51}$O$_6$N$_2$P<br>[495] | 0,16<br>CHCl$_3$/CH$_3$OH/H$_2$O<br>65 : 25 : 4 |
| CH$_2$—OH<br>CH—NH—C(=O)—R$_2$<br>CH$_2$—O—P(=O)(O$^\ominus$)—O—CH$_2$—CH$_2$—$^\oplus$N(CH$_3$)$_3$ | C$_{26}$H$_{51}$O$_6$N$_2$P<br>[519] | 0,12<br>CHCl$_3$/CH$_3$OH/H$_2$O<br>65 : 25 : 4 |

| formula | Lyso-cephalin analogs summation formula (MW) | Rf-value (running system) |
| --- | --- | --- |
| $\begin{array}{l} CH_2-NH-\overset{O}{\underset{\|}{C}}-R_1 \\ CH-OH \\ CH_2-O-\overset{O}{\underset{O^{\ominus}}{P}}-O-CH_2-CH_2-{}^{\oplus}NH_3 \end{array}$ | $C_{21}H_{45}O_6N_2P$ [453] | 0,36 $CHCl_3/CH_3OH/H_2O$ 65 : 25 : 4 |
| $\begin{array}{l} CH_2-OH \\ CH-NH-\overset{O}{\underset{\|}{C}}-R_2 \\ CH_2-O-\overset{O}{\underset{O^{\ominus}}{P}}-O-CH_2-CH_2-{}^{\oplus}NH_3 \end{array}$ | $C_{23}H_{45}O_6N_2P$ [477] | 0,30 $CHCl_3/CH_3OH/H_2O$ 65 : 25 : 4 |

$R_1$ = -palmityl
$R_2$ = -linolyl

It will be obvious to those skilled in the art that various changes may be made without departing from the scope of the invention and the invention is not to be considered limited to what is described in the specification.

What is claimed is:

1. A structural analog of natural phospholipids selected from the group consisting of compounds of the formulae:

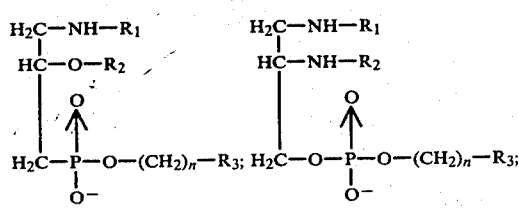

-continued

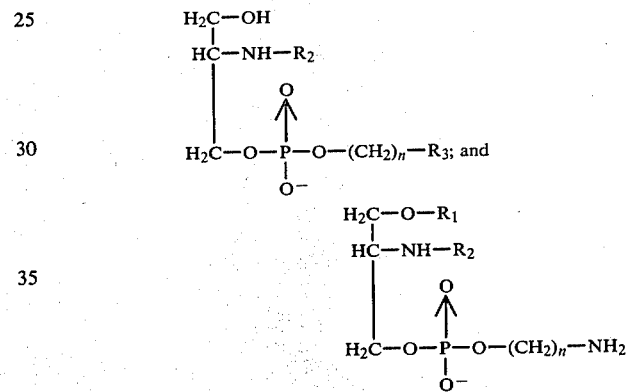

wherein $R_1$ and $R_2$ are either hydrogen and/or saturated or unsaturated straight-chain and branched anyl radicals with 2 to 24 C-atoms; $R_3$ is an amino group or a substituted amino group of the formula

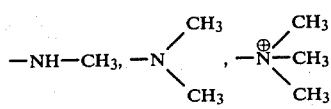

and n is 1–3.

2. A structural analog according to claim 1, characterized by the fact that the acyl radical or radicals are palmitic-, stearic-, oleic-, linoleic-, linolenic- or arachidonic acid radicals.

* * * * *